US00PP26319P2

(12) United States Plant Patent
Ault

(10) Patent No.: US PP26,319 P2
(45) Date of Patent: Jan. 19, 2016

(54) ***BAPTISIA* PLANT NAMED 'SPILLED BUTTERMILK'**

(50) Latin Name: ***Baptisia* hybrid**
Varietal Denomination: Spilled Buttermilk

(71) Applicant: James Robert Ault, Libertyville, IL (US)

(72) Inventor: James Robert Ault, Libertyville, IL (US)

(73) Assignee: CHICAGOLAND GROWS, INC, Glencoe, IL (US)

( * ) Notice: Subject to any disclaimer, the term of this patent is extended or adjusted under 35 U.S.C. 154(b) by 155 days.

(21) Appl. No.: 13/999,755

(22) Filed: Mar. 19, 2014

(51) Int. Cl.
*A01H 5/02* (2006.01)

(52) U.S. Cl.
USPC ..... Plt./263.1

(58) Field of Classification Search
USPC ..... Plt./263.1, 226
See application file for complete search history.

*Primary Examiner* — June Hwu
(74) *Attorney, Agent, or Firm* — Penny J. Aguirre

(57) ABSTRACT

A new cultivar of interspecific *Baptisia*, 'Spilled Buttermilk', that is characterized by its low growing plant habit that is wider than it is tall, its inflorescences held clear of the foliage that are slightly arching to horizontal at anthesis and becoming horizontal to pendulous as more flowers open, its second inflorescences with very densely borne flower buds, its flowers that are light yellow in color at anthesis and aging to a light green-white color, its foliage that is yellow-green to medium green in color, and its early bloom period beginning in early to mid-May in northern Illinois.

2 Drawing Sheets

Botanical classification: *Baptisia* hybrid.
'Spilled Buttermilk'.

BACKGROUND OF THE INVENTION

The present invention relates to a new and distinct cultivar of hybrid *Baptisia* plant, botanically known as *Baptisia* 'Spilled Buttermilk' and will be referred to hereafter by its cultivar name, 'Spilled Buttermilk'. The new cultivar represents a new false indigo, an herbaceous perennial grown for landscape use.

The new invention arose from an ongoing breeding program in a dedicated test plot in Glencoe, Ill. The objective of the breeding program is to develop novel interspecific hybrids of *Baptisia* that exhibit unique flower coloration, hybrid vigor, ease of clonal propagation, and desirable plant habits.

'Spilled Buttermilk' was selected as a single unique plant by the Inventor in May of 2007 after evaluating seedlings that derived from a cross made in May of 2004 between unnamed plants of hybrid *Baptisia* from the Inventor's breeding program. The female parent was a seedling that derived from open pollination of an unnamed interspecific hybrid of *Baptisia australis*×*Baptisia leucophaea*. The male parent was an unnamed plant in the Inventor's breeding program of *Baptisia leucophaea*.

Asexual propagation of the new cultivar was first accomplished by shoot tip cuttings under the direction of the Inventor in July of 2007 in Glencoe, Ill. Asexual propagation by shoot tip cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Spilled Buttermilk' as a unique cultivar of *Baptisia*.

1. 'Spilled Buttermilk' exhibits a low growing plant habit that is wider than it is tall when mature.
2. 'Spilled Buttermilk' exhibits inflorescences held clear of the foliage that are slightly arching to horizontal at the beginning of anthesis and becoming horizontal to pendulous as more flowers open.
3. 'Spilled Buttermilk' exhibits secund inflorescences with very densely borne flower buds.
4. 'Spilled Buttermilk' exhibits flowers that are light yellow in color at anthesis and aging to a light green-white color.
5. 'Spilled Buttermilk' exhibits foliage that is yellow-green to medium green in color.
6. 'Spilled Buttermilk' exhibits an early bloom period beginning in early to mid-May in northern Illinois.

The female parent of 'Spilled Buttermilk' differs from 'Spilled Buttermilk' in having inflorescences that are held upright, in having flowers that are blue-violet with a light yellow keel in color, and in having flowers that are radially dispersed around the inflorescence. The male parent differs from 'Spilled Buttermilk' in having flowers that are cream colored with hints of yellow, in having conspicuously pubescent stems and foliage, and in having foliage that is grey-green in color. 'Spilled Buttermilk' can be most closely compared to the cultivars *Baptisia*×*bicolor* 'Starlite' (U.S. Plant Pat. No. 19,971) and *Baptisia* 'Mojito' (U.S. Plant Pat. No. 25,987). Both cultivars are similar to 'Spilled Buttermilk' in having early bloom periods and 'Mojito' also similar to 'Spilled Buttermilk' in having flowers that are yellowish in color. 'Starlite' differs from 'Spilled Buttermilk' in having flowers that are lavender to blue in color with a yellow keel, in having upright to leaning inflorescences, in having inflorescences that are partially hidden in the foliage, and in having a plant habit that is denser and larger. 'Mojito' differs from 'Spilled Buttermilk' in having a longer (4-week) bloom period, in having upright inflorescences, in having foliage that is deeper yellow-green in color, and in being taller and wider in size.

BRIEF DESCRIPTION OF THE DRAWINGS

The accompanying colored photographs illustrate the overall appearance and distinct characteristics of the new *Baptisia*. The photographs in FIG. 1 and FIG. 3 were taken of a plant three years in age and the photograph in FIG. 2 was taken of a plant four years in age. The plants in all the photographs were grown outdoors in a trial plot in Glencoe, Ill.

The photograph in FIG. 1 provides a close-up view of an inflorescence of 'Spilled Buttermilk'.

Figure 1:
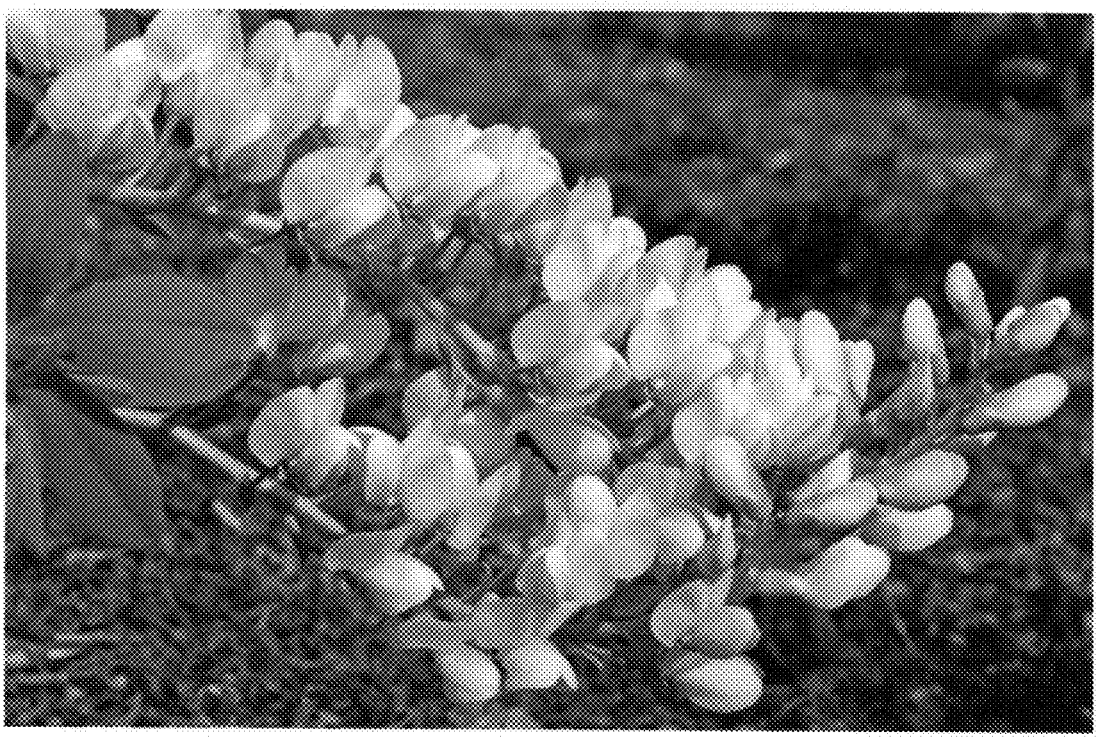
Figure 2:
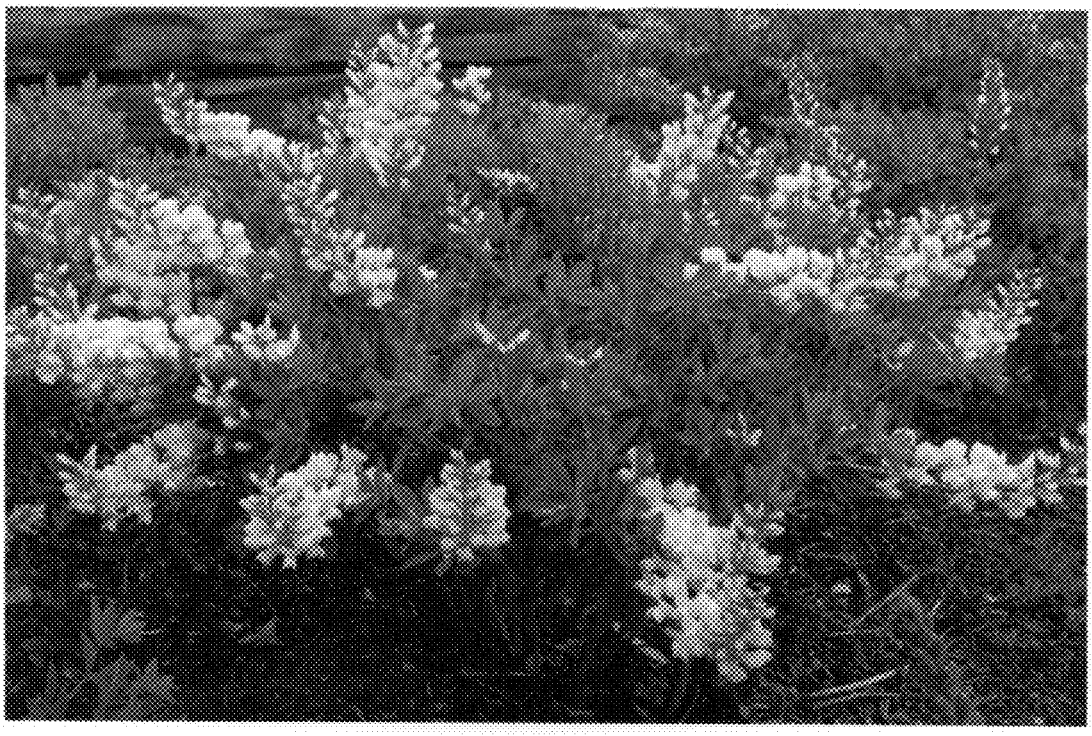

The photograph in FIG. 2 provides a side view of 'Spilled Buttermilk' in bloom and illustrates the plant habit in bloom.

Figure 3:
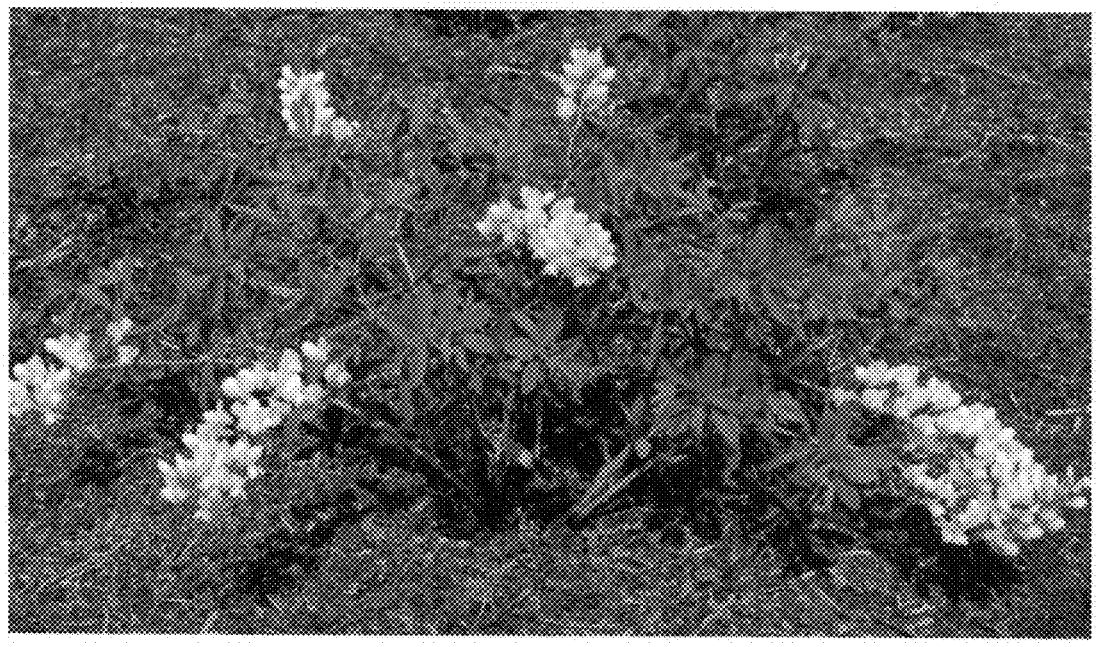

The photograph in FIG. 3 provides a side view of a younger plant of 'Spilled Buttermilk'. The colors in the photographs are as close as possible with the photographic and printing technology utilized and the color values cited in the detailed botanical description accurately describe the colors of the new *Baptisia*.

DETAILED BOTANICAL DESCRIPTION OF THE PLANT

The following is a detailed description of 6 year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

- *Blooming period*.—Three weeks from May to early June in northern Illinois (U.S.D.A. Zone 5).
- *Plant habit*.—Low growing and open, wider than it is tall with inflorescences held clear of the foliage that are slightly arching to horizontal at the beginning of anthesis and becoming horizontal to pendulous as more flowers open.
- *Height and spread*.—A six year old plant produces 18 stems and reaches 36 cm in height and 97 cm in width (vegetative growth).
- *Hardiness*.—U.S.D.A. Zones 5 to 7.
- *Diseases and pests*.—No susceptibility or resistance to diseases or pests has been observed.
- *Root description*.—Deep rooted, fibrous.
- *Propagation*.—Shoot tip cuttings.
- *Growth rate*.—Moderate.

Stem description:

- *Branch habit*.—Moderately branched; average of 18 branches with an average of 2 secondary branches, and 2 tertiary branches.
- *Stem size*.—Main stem; average of 36 cm (including peduncle) in length and 5 mm in width, secondary; average of 28 cm in length and 4 mm, tertiary; an average of 5.2 cm in length and 2 mm in width.
- *Stem shape*.—Oval.
- *Stem color*.—144A.
- *Stem surface*.—Hairless, satiny but slightly glaucous with ridges.

Foliage description:

- *Leaf shape*.—Fan-shaped in overall outline.
- *Leaf division*.—3-palmate.
- *Leaf internode*.—Foliage begins 8 cm from base, an average of 4 cm on main stem and an average of 4 cm on secondary branches.
- *Leaf size*.—Average 6.5 cm in length and 11.5 cm in width when mature.
- *Leaf quantity*.—About 44 per stem.
- *Leaflet shape*.—Oblanceolate.
- *Leaflet base*.—Cuneate.
- *Leaflet apex*.—Acute.
- *Leaflet venation*.—Pinnate pattern, not conspicuous, color matches leaflet color on the upper and lower surface with the mid rib of lower surface N137C.
- *Leaflet margins*.—Entire.
- *Leaf attachment*.—Petiolate.
- *Leaf arrangement*.—Alternate.
- *Leaflet surface*.—Glabrous and slightly glaucous on upper and lower surface.
- *Leaflet color*.—Newly expanded; upper and lower surface 144A, mature; upper and lower surface; N137D.
- *Leaflet size*.—An average of 6.5 cm in length and 2.5 cm in width.
- *Petioles*.—Average of 6 mm in length and 2 mm in width, clasping to stem at mature nodes, 147C in color, surface is glabrous and satiny.
- *Stipules*.—Lanceolate in shape, base is truncate to stem, apex is narrowly acute to acuminate, up to 2.4 cm in length and 8 mm in width on mature leaves, N137D in color on upper and lower surface, glabrous on upper and lower surface.

Flower description:

- *Inflorescence type*.—Terminal racemes of pea-like flowers on main and secondary branches, blooms from the base to the apex, inflorescences secund; buds produced only on one side of the inflorescences.
- *Inflorescence size*.—Average of 26 cm in length and 5.5 cm in width in mid section.
- *Lastingness of inflorescence*.—About 21 days.
- *Flower size*.—About 1.8 cm in depth and about 2.1 cm in diameter.
- *Flower fragrance*.—Medium fragrance.
- *Flower number per inflorescence*.—Average of 37 to 40.
- *Peduncle*.—Oval in shape, up to 6 cm in length and an average of 1 cm in width, 146D in color, surface is glabrous, satiny and slightly glaucous with ridges, flower internode length averages 1 cm.
- *Pedicel*.—About 1 cm in length, about 1 mm in width, oval in shape, ranges between 200A and 146B, glabrous and satiny surface.
- *Flower buds*.—Kidney-shaped, 1.3 cm in length and 1 cm in width, petal portion is 160C in color, calyx portion same as open flowers.
- *Flower type*.—Papilionaceous, held at about a 20° angle.
- *Calyx*.—Campanulate, about 5 mm and 5 mm in diameter, surface is glabrous and satiny, blend, of 144A, persistent.
- *Sepals*.—4, fused with the exception of apex of each, free portion is triangular in shape 2 mm in width and 2 mm in depth with an acute apex, 144A.
- *Corolla features*.—Papilionaceous (4 segments) with a reflexed banner, 2 lateral wings and a concealed keel, lateral wings; oblong in shape, about 2 cm in length and 1.5 cm in width, color on outer surface and the inner surface is 2D aging to 157A, rounded apex, oblique base keel; not visible, comprised of 2 segments surrounding reproductive organs, oblong (slightly oblique) in shape with rounded apex and oblique base, 2 cm in length and 1.5 cm in width, upper surface and lower surface are 2D aging to 157A in color, segments joined at center point, banner; orbicular and strongly reflexed in shape, about 2 cm in length and 1.5 cm in width, 2D, aging to 157A in color, with mid region having a base of 150C, apex is rounded with a single notch, surface is glabrous on all sections.

*Receptacle*.—Disk-shaped, gelatinous, 149A in color, about 5 mm in diameter and 2 mm in depth.

Reproductive organs:

*Gynoecium*.—1 Pistil, about 2 cm in length, 1.5 mm in width; style is 143B in color and 8 mm in length; stigma minute, too small to read color, ovary is superior with a stipe, 143C in color, 1 cm in length and 2 mm in width; stipe is 143C in color, 4 mm in length and 15 mm in width.

*Androcoecium*.—10 stamens, not united, 2.5 cm in length and 1 mm in width; filament is 2 cm in length, 1 mm in width and 157A in color; anther is dorsifixed, 2 mm in length and 1 mm in width and 200A in color, pollen is moderate in quantity and 23A in color.

*Fruit*.—An inflated pod, technically a legume, 0 to 1 produced per inflorescence (open-pollinated), elliptic and slightly oblong in shape, average of 3.5 cm in length by 1.6 cm in width with a beak approx. 1.5 cm in length, color of outer surface is a blend of 202A and N200B, color of inner surface when mature is a blend of N199B and 202A, walls 1.5 mm and hard at maturity, seed; average of 3 per fruit (open-pollinated), 160B in color, oval with the hilum side more or less straight, seed compressed to flattish, 4 mm in length, 3 mm in width and 2 mm in thickness.

It is claimed:

1. A new and distinct cultivar of *Baptisia* plant named 'Spilled Buttermilk' as herein illustrated and described.

* * * * *